United States Patent [19]

Takesue et al.

[11] Patent Number: 5,728,500
[45] Date of Patent: Mar. 17, 1998

[54] ELECTROPHOTOGRAPHIC PHOTORECEPTOR WITH ACENAPHTHENE COMPOUND

[75] Inventors: Atsushi Takesue; Mitsutoshi Anzai; Takanobu Watanabe; Chieko Inayoshi, all of Tsukuba, Japan

[73] Assignee: Hodogaya Chemical Co., Ltd., Kawasaki, Japan

[21] Appl. No.: 683,380

[22] Filed: Jul. 18, 1996

[30] Foreign Application Priority Data

Jul. 21, 1995 [JP] Japan ................... 7-206761
Feb. 9, 1996 [JP] Japan ................... 8-046844

[51] Int. Cl.$^6$ ................ G03G 5/09; G03G 5/06
[52] U.S. Cl. .......................... 430/83; 430/59
[58] Field of Search ................ 430/59, 73, 83

[56] References Cited

U.S. PATENT DOCUMENTS

| | | | |
|---|---|---|---|
| 5,053,302 | 10/1991 | Makino et al. | 430/59 |
| 5,098,809 | 3/1992 | Kikuchi et al. | 430/83 |
| 5,238,765 | 8/1993 | Senoo et al. | 430/59 |
| 5,534,375 | 7/1996 | Kaneko et al. | 430/59 |

*Primary Examiner*—Roland Martin
*Attorney, Agent, or Firm*—Oblon, Spivak, McClelland, Maier & Neustadt, P.C.

[57] ABSTRACT

An acenaphthene compound of the following formula (1).

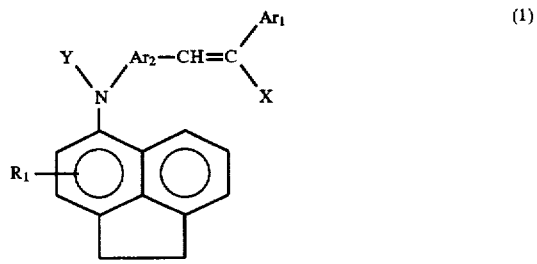

wherein $Ar_1$ is an aryl group which may have a substituent; $Ar_2$ is a phenylene, naphthylene, biphenylene or anthrylene group which may have a substituent; $R_1$ is a hydrogen atom, a lower alkyl group or a lower alkoxy group; X is a hydrogen atom, an alkyl group which may have a substituent or an aryl group which may have a substituent; and Y is an aryl group which may have a substituent or a group of the formula (2).

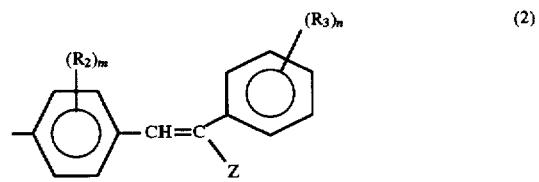

wherein $R_2$ is a hydrogen atom, a lower alkyl group or a lower alkoxy group, $R_3$ is a hydrogen atom, a halogen atom or a lower alkyl group, Z is a hydrogen atom or an aryl group which may have a substituent, and m and n are an integer of from 0 to 4.

14 Claims, 2 Drawing Sheets

ELECTROPHOTOGRAPHIC PHOTORECEPTOR WITH ACENAPHTHENE COMPOUND

BACKGROUND OF THE INVENTION

1. Field of the Invention

The present invention relates to a novel acenaphthene compound and an electrophotographic photoreceptor having a photosensitive layer containing such an acenaphthene compound. The novel acenaphthene compound of the present invention is useful as a charge-transporting material used in an electrophotographic photoreceptor or an organic electroluminescent device.

2. Discussion of Background

The electrophotographic system is one of image-forming methods, wherein the surface of a photoreceptor employing a photoconductive material is electrified, for example, by corona discharge and subjected to exposure to selectively dissipate the charge at the exposed portion to obtain an electrostatic latent image, which is then developed by a toner, and transferred to e.g. a paper sheet, followed by fixing to obtain an image.

The photoreceptor may be an inorganic photoreceptor composed mainly of an inorganic photoconductive compound such as selenium, zinc oxide, cadmium sulfide or silicon, or an organic photoreceptor employing an organic compound having a charge-generating material and a low molecular weight or high molecular weight charge-transporting material dispersed in a binder resin. Inorganic photoreceptors have many merits respectively and have been widely used. However, for example, selenium has drawbacks such that the production conditions are difficult, the production costs are high, and it is weak against heat or mechanical shock and likely to undergo crystallization, whereby the properties tend to deteriorate. Zinc oxide and cadmium sulfide have a problem with respect to the moisture resistance or mechanical strength and have a drawback that they undergo deterioration due to exposure or electrification of a dye incorporated as a sensitizer, whereby no adequate durability can be obtained. Also silicon has problems that the production conditions are difficult, and the production costs are high since highly irritating gas is used, and since it is sensitive to humidity, its handling requires a special care.

In recent years, for the purpose of overcoming such drawbacks inherent to these inorganic photoreceptors, organic photoreceptors employing various organic compounds have been studied and widely used. The organic photoreceptor includes a single layer type photoreceptor having a charge-generating material and a charge-transporting material dispersed in a binder resin and a laminated layer type photoreceptor having a charge-generating layer and a charge-transporting layer laminated to have separate functions. The function-separated type organic photoreceptor has been extensively studied and widely used for such reasons that a wide range of choice of the respective materials is available, and a photoreceptor having optional performance can relatively easily be prepared by a proper combination.

As the charge-generating material, many organic pigments or dyes have been proposed and practically used, including, for example, azo compounds, bisazo compounds, trisazo compounds, tetrakis azo compounds, thiapyrylium salts, squarilium salts, azulenium salts, cyanine dyes, perylene compounds, non-metal or metal phthalocyanine compounds, polycyclic quinone compounds, thioindigo compounds, and quinacridone compounds.

The charge-transporting material includes, for example, oxadiazole compounds disclosed in Japanese Examined Patent Publication No. 5466/1959, oxazole compounds disclosed in Japanese Unexamined Patent Publication No. 123544/1981, pyrazoline compounds disclosed in Japanese Examined Patent Publication No. 41880/1977, hydrazone compounds disclosed in Japanese Examined Patent Publications No. 42380/1980, No. 40104/1986, No. 35673/1987 and No. 35976/1988, diamine compounds disclosed in Japanese Examined Patent Publication No. 32372/1983, stilbene compounds disclosed in Japanese Examined Patent Publications No. 18738/1988, No. 19867/1988 and No. 39306/1991, and butadiene compounds disclosed in Japanese Unexamined Patent Publication No. 30255/1987. Organic photoreceptors employing these charge-transporting materials have excellent properties, and some of them are practically used. However, there has been none which fully satisfies various properties required for a photoreceptor for an electrophotographic system.

The charge-transporting material to be used for the organic photoreceptor, is required to satisfy various properties as a photoreceptor including the sensitivity and to have chemical stability so that it is durable against light, ozone or an electrical load as well as stability and durability so that the sensitivity will not deteriorate by repeated use or use for a long period of time.

SUMMARY OF THE INVENTION

It is an object of the present invention to provide a novel acenaphthene compound useful as such a charge-transporting material having performances which fully satisfy properties required for an electrophotographic photoreceptor.

Another object of the present invention is to provide a electrophotographic photoreceptor which satisfies the properties required for a photoreceptor and which has high sensitivity and high durability.

The present invention provides a novel acenaphthene compound of the following formula (1).

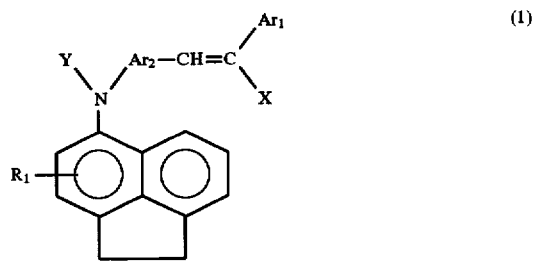

wherein $Ar_1$ is an aryl group which may have a substituent; $Ar_2$ is a phenylene, naphthylene, biphenylene or anthrylene group which may have a substituent; $R_1$ is a hydrogen atom, a lower alkyl group or a lower alkoxy group; X is a hydrogen atom, an alkyl group which may have a substituent or an aryl group which may have a substituent; and Y is an aryl group which may have a substituent or a group of the formula (2).

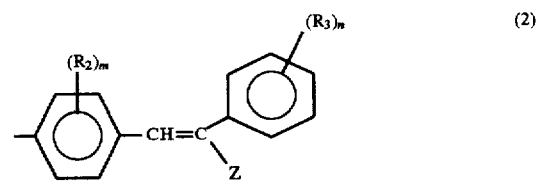

wherein $R_2$ is a hydrogen atom, a lower alkyl group or a lower alkoxy group, $R_3$ is a hydrogen atom, a halogen atom or a lower alkyl group, Z is a hydrogen atom or an aryl group which may have a substituent, and m and n are an integer of from 0 to 4.

Further, the present invention provides an electrophotographic photoreceptor having a photosensitive layer which contains the novel acenaphthene compound as defined above.

DETAILED DESCRIPTION OF THE INVENTION

Figure 1:
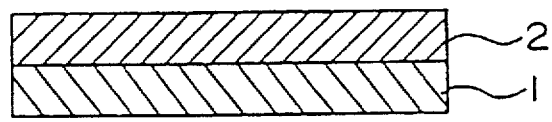
FIG. 1 is a cross-sectional view of a single layer electrophotographic photoreceptor.

The acenaphthene compound of the formula (1) of the present invention is a novel compound, and such a compound can be synthesized by subjecting a corresponding amino compound to N-arylating reaction such as Ullmann reaction to prepare a triarylamine compound, formylating the triaryl amine compound thus prepared and further reacting the formylation product with a corresponding phosphonic acid ester by Horner-Emmons-Wittig reaction. The formylation reaction is generally conducted in accordance with Vilsmeier reaction.

For example, a diarylamine compound of the formula (3),

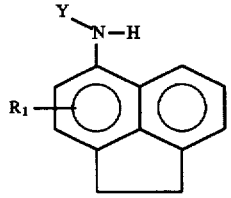

(wherein $R_1$ and Y are as defined with regard to the above formula (1)) and a halogenated aryl compound of the formula (4),

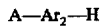

A—$Ar_2$—H      (4)

(wherein $Ar_2$ is as defined with regard to the formula (1) and A is a chlorine atom, a bromine atom or an iodine atom) are subjected to a condensation reaction to prepare a triarylamine compound of the formula (5),

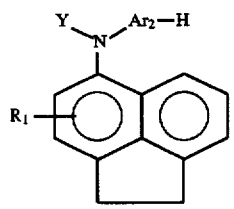

(wherein $Ar_2$, $R_1$ and Y are as defined with regard to the formula (1)), and the triarylamine compound thus prepared is formylated with N,N-dimethylformamide and phosphorus oxychloride to prepare an aldehyde compound of the formula (6),

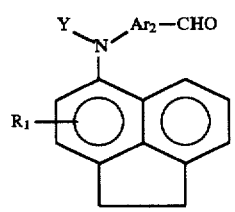

(wherein $Ar_2$, $R_1$ and Y are as defined with regard to formula (1)).

Thereafter, the aldehyde compound thus prepared is reacted with a phosphonic acid ester of the formula (7),

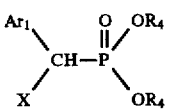

(wherein $A_r$, X are as defined with regard to the formula (1), and $R_4$ is a lower alkyl group) to prepare an acenaphthene compound of the formula (1) of the present invention.

Also, in the production of an acenaphthene compound of the formula (1) of the present invention, an acenaphthene compound of the formula (1) of the present invention, wherein Y is a group of the formula (2),

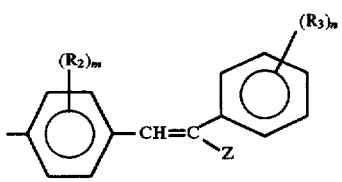

is obtained by formylating a N-arylaniline compound of the formula (8),

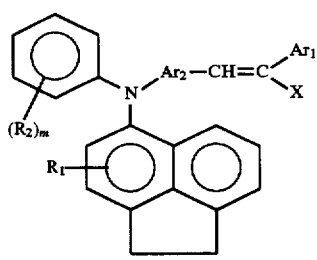

(wherein $Ar_1$, $Ar_2$, $R_1$, $R_2$, X and m are as defined with regard to the formulas (1) and (2)) as a starting material in the same manner as above to prepare an aldehyde compound of the formula (9),

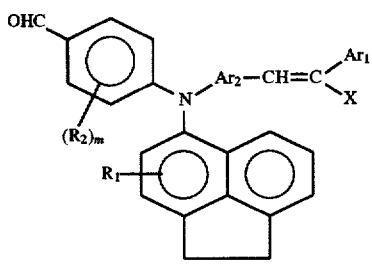

(9)

(wherein $Ar_1$, $Ar_2$, $R_1$, $R_2$, X and m are as defined with regard to the formulas (1) and (2)) and further reacting the aldehyde compound with a phosphonic acid ester of the formula (10),

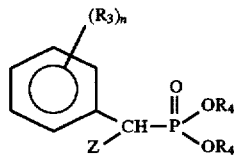

(10)

(wherein $R_3$, $R_4$, Z and n are as defined with regard to the formula (1)).

The condensation reaction of the above diarylamine compound and halogenated aryl compound and the like is known as Ullmann reaction, and is conducted in the presence or absence of a solvent. Examples of the solvent include high boiling solvents such as nitrobenzene, dichlorobenzene and dimethylsulfoxide. Examples of a basic compound used include potassium carbonate, sodium carbonate, sodium hydrogen carbonate, potassium hydroxide and sodium hydroxide. Also, this reaction is conducted in the presence of a catalyst such as copper powder, halogenated copper or the like. The reaction temperature is usually from 160° to 230° C.

The condensation reaction of the above aldehyde compound and phosphonic acid ester is known as Horner-Emmons-Wittig reaction, and is conducted preferably in the presence of a basic catalyst.

Examples of the basic catalyst include potassium hydroxide, sodium amide, sodium methylate, potassium-t-butoxide and the like. Examples of the solvents include methyl alcohol, ethyl alcohol, t-butyl alcohol, toluene, tetrahydrofurane, dioxane, dimethylsulfoxide, N,N-dimethylformamide and the like. The reaction temperature is usually from room temperature to 100° C.

A phosphonic acid ester of the formula (7) or (10) used as a starting material in the present invention, can be easily synthesized by heat-reacting a corresponding halogen compound with trialkyl phosphite directly or in an organic solvent such as toluene, xylene, N,N-dimethylformamide or the like.

In the above formula (1), when $Ar_1$ is an aryl group having a substituent, examples of the substituent include a $C_{1-4}$ lower alkyl group, a $C_{1-4}$ lower alkoxy group, a $C_{5-6}$ cycloalkyl group, a benzyl group, a phenyl group or a halogen atom. When the substituent is the lower alkyl group or the lower alkoxy group, it may be further substituted with a $C_{1-4}$ lower alkoxy group or a halogen atom, and when the substituent is the benzyl group or the phenyl group, it may be further substituted with a $C_{1-4}$ lower alkyl group, a $C_{1-4}$ lower alkoxy group or a halogen atom. Examples of the aryl group for $Ar_1$ include a phenyl group, a naphthyl group, a biphenylyl group, an anthryl group, a pyrenyl group and the like.

When $Ar_2$ is a phenylene group, a naphthylene group, a biphenylene group or an anthrylene group, which has a substituent, examples of the substituent include a $C_{1-4}$ lower alkyl group, a $C_{1-4}$ lower alkoxy group or a halogen atom, and when the substituent is the lower alkyl group or the lower alkoxy group, it may be further substituted with a $C_{1-4}$ alkoxy group or a halogen atom.

When X, Y or Z is an aryl group having a substituent, examples of the substituent may be the same as the above-mentioned substituent of $Ar_1$. When X is an alkyl group having a substituent, examples of the substituent include a $C_{1-4}$ lower alkoxy group, a $C_{5-6}$ cycloalkyl group, a halogen atom and the like. Examples of the aryl group of X, Y or Z include a phenyl group, a naphthyl group, a biphenylyl group, an anthryl group, a pyrenyl group and the like.

The following compounds may be mentioned as specific examples of the acenaphthene compound of the formula (1) of the present invention.

Compound No. (1)

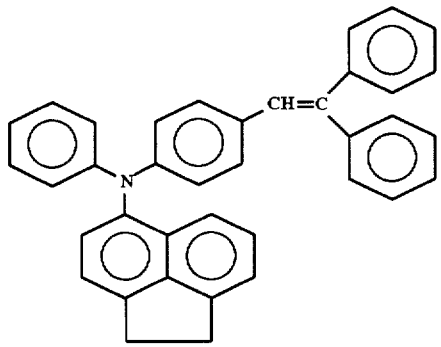

-continued
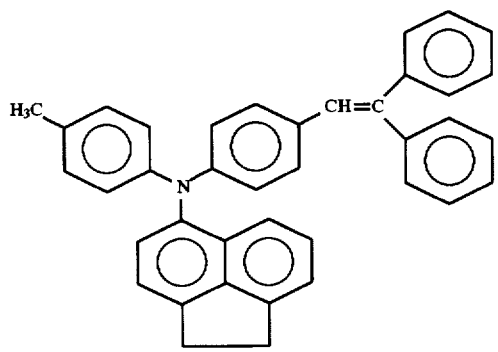
Compound No. (2)
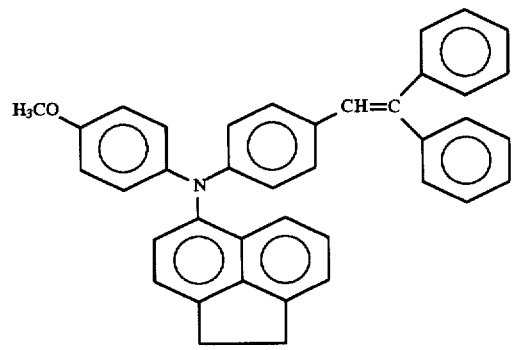
Compound No. (3)
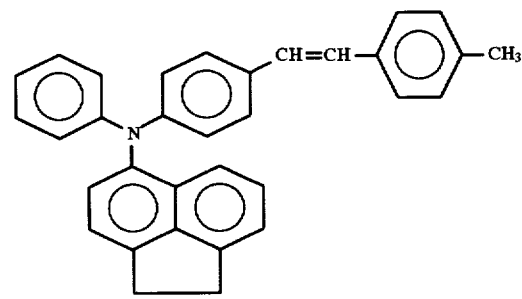
Compound No. (4)
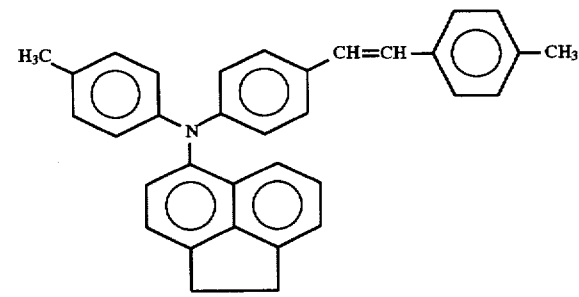
Compound No. (5)
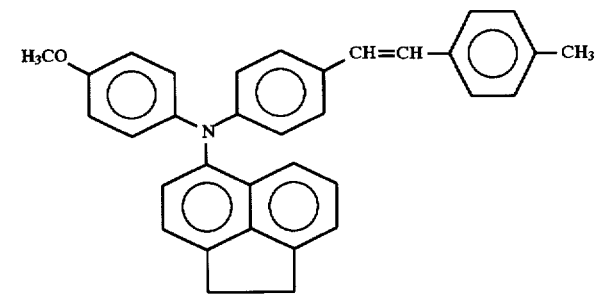
Compound No. (6)

-continued
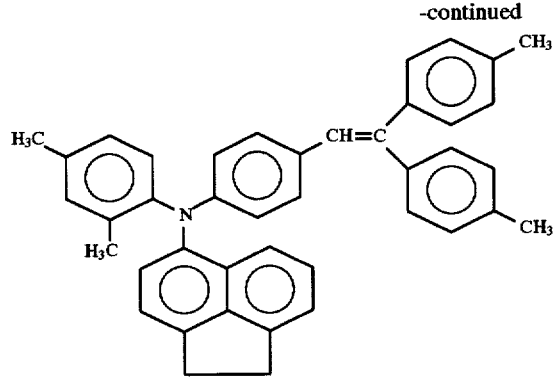
Compound No. (7)
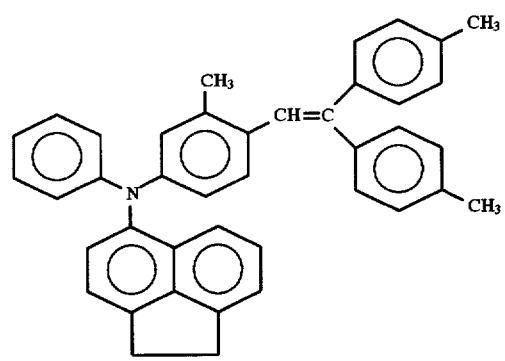
Compound No. (8)
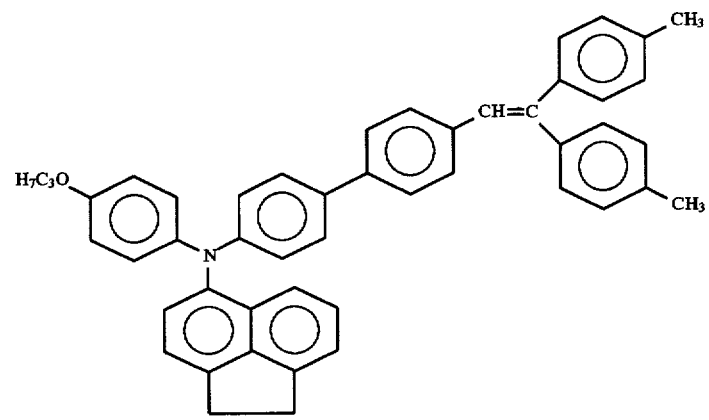
Compound No. (9)
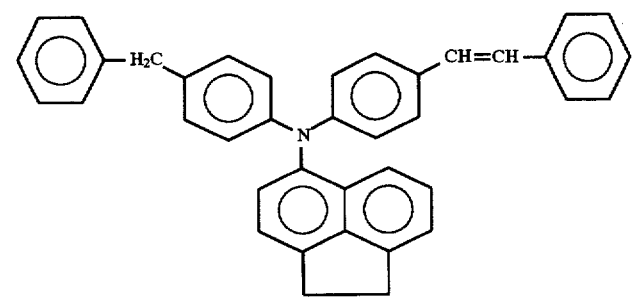
Compound No. (10)

-continued
Compound No. (11)
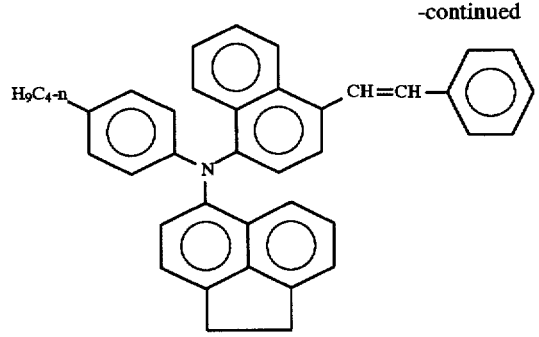
Compound No. (12)
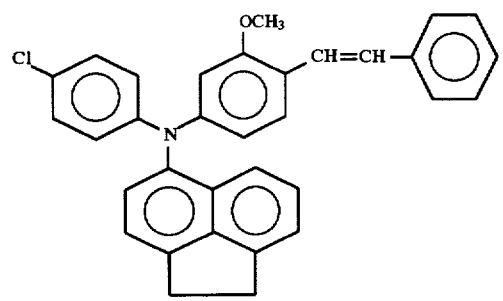
Compound No. (13)
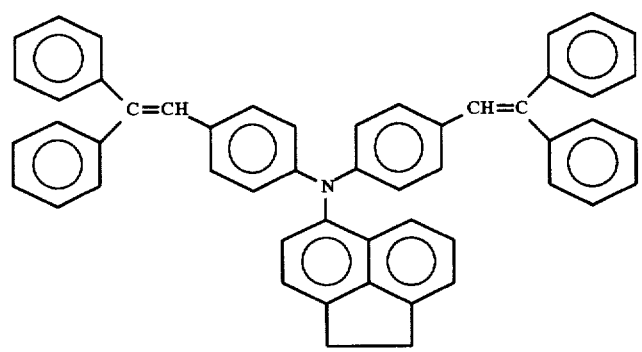
Compound No. (14)
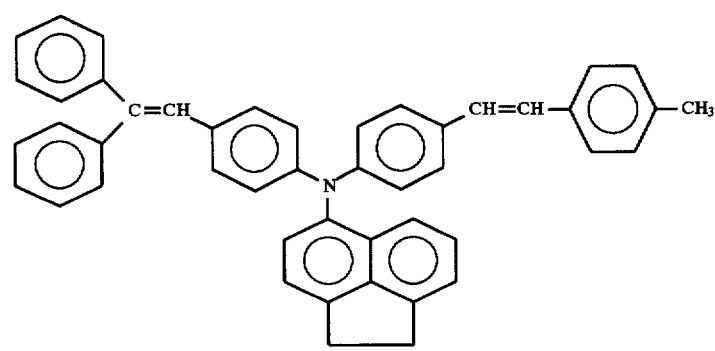
Compound No. (15)
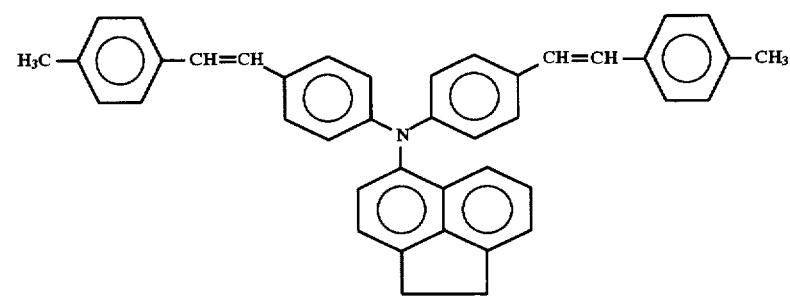
The electrophotographic photoreceptor of the present invention has a photosensitive layer containing one or more of the above-mentioned acenaphthene compounds. Various forms are available for the photosensitive layer, and any one of them may be employed for the photosensitive layer of the electrophotographic photoreceptor of the present invention. Typical examples of such photoreceptors are shown in FIGS. 1 to 5.

The photoreceptor shown in FIG. 1 is the one wherein a photosensitive layer 2 comprising an acenaphthene compound, a sensitizing dye and a binder resin, is formed on an electrically conductive support 1.

Figure 2:
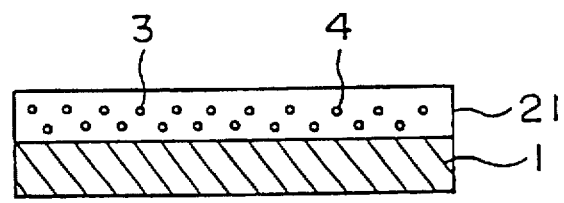
FIG. 2 is a cross-sectional view of a single layer electrophotographic photoreceptor having a charge-generating material dispersed therein.

The photoreceptor shown in FIG. 2 is the one wherein a photosensitive layer 21 having a charge-generating material 4 dispersed in a charge-transporting medium 3 comprising an acenaphthene compound and a binder resin, is formed on an electrically conductive support 1. With this photoreceptor, a charge carrier is generated when the charge-generating material absorbs light, and the charge carrier is transported by the charge-transporting medium. Here, the charge-transporting material should preferably be transparent to the light for generating the charge carrier. The acenaphthene compound of the present invention shows no substantial absorption in a visible wavelength region and thus satisfies a condition that the absorption wavelength region does not overlap with the absorption wavelength region of the charge-generating material.

Figure 3:
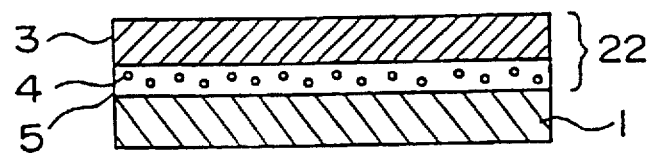
FIG. 3 is a cross-sectional view of a electrophotographic photoreceptor having a charge-generating layer and a charge-transporting layer laminated in this order on an electrically conductive support.

The photoreceptor shown in FIG. 3 is the one wherein a photosensitive layer 22 composed of a lamination of a charge-generating layer 5 containing a charge-generating material 4 as the main component and a charge-transporting layer 3 comprising an acenaphthene compound and a binder resin, is formed on an electrically conductive support 1. With this photoreceptor, light passed through the charge-transporting layer 3 reaches the charge-generating layer 5, whereupon it is absorbed by the charge-generating material 4, whereby a charge carrier is generated. This charge carrier is injected into and transported by the charge-transporting layer 3.

Figure 4:
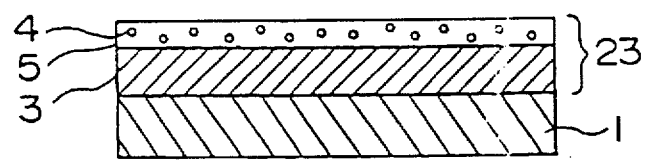
FIG. 4 is a cross-sectional view of a electrophotographic photoreceptor having a charge-transporting layer and a charge-generating layer laminated in this order on an electrically conductive support.

The photoreceptor shown in FIG. 4 is the one wherein a photosensitive layer 23 is formed with the order of lamination of the charge-generating layer 5 and the charge-transporting layer 3 of the photoreceptor in FIG. 3 reversed. The generation and transportation of a charge carrier may be explained by the same mechanism as described above.

Figure 5:
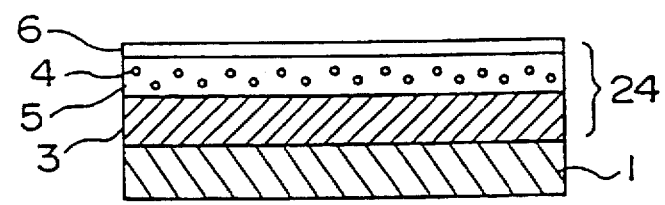
FIG. 5 is a cross-sectional view of a electrophotographic photoreceptor provided with a protective layer.

The photoreceptor shown in FIG. 5 is the one wherein a photosensitive layer 24 is formed with a protective layer 6 further laminated on the charge-generating layer 5 of the photoreceptor of FIG. 4 for the purpose of improving the mechanical strength.

As illustrated in the foregoing, the photoreceptor of the present invention can be prepared by conventional methods. For example, it may be prepared by coating on an electrically conductive support a coating solution prepared by adding a charge-generating material, a sensitizing dye, an electron attractive compound, a plasticizer, a pigment, other additives, as the case requires to a solution having an acenaphthene compound of the formula (1) dissolved in a suitable solvent together with a binder resin, followed by drying to form a photosensitive layer having a thickness of from a few μm to a few tens μm. In the case of a photosensitive layer comprising two layers of a charge-generating layer and a charge-transporting layer, it may be prepared by coating the above coating solution on a charge-generating layer, or by forming a charge-generating layer on a charge-transporting layer obtained by coating the above coating solution. Further, the photoreceptor thus prepared, may further be provided with an adhesive layer, an interlayer or a barrier layer, as the case requires.

The amount of the acenaphthene compound in the photosensitive layer of a single layer type photoreceptor or in a charge-transporting layer of a laminated layer type photoreceptor, is usually from 30 to 70%, preferably from 40 to 60%, by weight.

The solvent to be used for the preparation of the coating solution may, for example, be a polar organic solvent such as tetrahydrofuran, 1,4-dioxane, methyl ethyl ketone, cyclohexanone, acetonitrile, N,N-dimethylformamide or ethyl acetate, an aromatic organic solvent such as toluene or xylene, or a chlorinated hydrocarbon solvent such as dichloromethane or dichloroethane. A solvent providing a good solubility to the acenaphthene compound and the binder resin is preferably employed.

The sensitizing dye may, for example, be a triarylmethane dye such as methyl violet, brilliant green, crystal violet or acid violet, a xanthene dye such as Rhodamine B, Eosine S or Rose Bengale, a thiazine dye such as methylene blue, a pyrylium dye such as a benzopyrylium salt, a thiapyrylium dye, or a cyanine dye.

The electron attractive compound which is capable of forming a charge transfer complex with the acenaphthene compound may, for example, be a quinone such as chloranil, 2,3-dichloro-1,4-naphthoquinone, 1-nitroanthraquinone, 2-chloroanthraquinone or phenanthrenequinone, an aldehyde such as 4-nitrobenzaldehyde, a ketone such as 9-benzoylanthracene, indandione, 3,5-dinitrobenzophenone, 2,4,7-trinitrofluorenone or 2,4,5,7-tetranitrofluorenone, an acid anhydride such as phthalic anhydride or 4-chloronaphthalic anhydride, a cyano compound such as tetracyanoethylene, terephthalal malenonitrile or 9-anthrylmethylidene malenonitrile, or a phthalide such as 3-benzalphthalide, 3-(α-cyano-p-nitrobenzal)-4,5,6,7-tetrachlorophthalide.

As the binder resin, various resins which are compatible with an acenaphthene compound may be mentioned including polymers and copolymers of vinyl compounds such as styrene, vinyl acetate, vinyl chloride, an acrylic acid ester, a methacrylic acid ester and butadiene, polyvinyl acetal, polycarbonate, polyester, polyphenylene oxide polyurethane, cellulose ester, a phenoxy resin, a silicone resin, and an epoxy resin. The amount of the binder resin is usually within a range of from 0.4 to 10 parts by weight, preferably from 0.5 to 5 parts by weight, per part by weight of the acenaphthene compound.

Further, the photosensitive layer of the present invention may contain a conventional plasticizer for the purpose of improving the film-forming property, flexibility and mechanical strength. As such a plasticizer, a phthalic acid ester, a phosphoric acid ester, chlorinated paraffin, methyl naphthalene, an epoxy compound or a chlorinated fatty acid ester may, for example, be mentioned.

As the electrically conductive support on which the photosensitive layer is formed, a material which is commonly used for conventional photoreceptors for electrophotography, may be employed. For example, a drum or sheet made of a metal such as aluminum, stainless steel or copper, or a laminate or vapor deposited product of such metals, or a plastic film, a plastic drum, paper or a paper tube treated for electrical conduction by coating a conductive material such as a metal powder, carbon black, copper iodide or a polymer electrolyte together with a proper binder, or a plastic film or plastic drum having electrical conductivity imparted by incorporating a conductive material, may be mentioned.

Now, the present invention will be described in further detail with reference to Examples. However, it should be understood that the present invention is by no means restricted by such specific Examples.

In the following Examples, "part" means "part by weight" and concentrations are expressed by "wt%".

PREPARATION EXAMPLE 1 (Preparation of Compound No. 1)

Preparation of 5-(N,N-diphenylamino)acenaphthene 33.85 g (0.2 mol) of 5-aminoacenaphthene was mixed with 102.1 g (0.5 mol) of iodo benzene, 1.3 g (0.02 mol) of copper powder, 34.5 g (0.25 mol) of anhydrous potassium carbonate and 100 ml of nitrobenzene, and the mixture was stirred at 200° C. for 26 hours. The reaction was determined to be finished when disappearance of 5-aminoacenaphthene and 5-(N-phenylamino)acenaphthene as an intermediate was identified. 300 ml of toluene was added thereto to dissolve a product, and the resultant mixture was filtrated and concentrated. The concentrated product was purified by column chromatography (carrier: silica gel, eluent: toluene/hexane= ¼) to obtain 48.7 g (yield: 75.7%, melting point: 168.5°–170.5° C.) of 5-(N,N-diphenylamino)acenaphthene.

Preparation of 5-[N-(4-formylphenyl)-N-phenylamino]acenaphthene 32.14 g (0.1 mol) of the above prepared 5-(N,N-diphenylamino)acenaphthene was dissolved in 300 ml of N,N-dimethylformamide, and 22.73 g (0.15 mol) of phosphorus oxychloride was dropwise added thereto at room temperature for 30 minutes. After raising the temperature to 50° C., the reaction mixture was stirred for 14 hours. The reaction was determined to be finished when disappearance of 5-(N,N-diphenylamino)acenaphthene was identified. The reaction product was poured into an aqueous solution having 45 g (1.05 mol) of 93% sodium hydroxide dissolved in 1000 ml of water. The resultant mixture was cooled to precipitate a crystal, and the crystal was filtrated, washed with water and dried to obtain 30.27 g (yield: 86.6%, melting point: 138.0°–141.0° C.) of 5-[N-(4-formylphenyl)-N-phenylamino]acenaphthene.

Preparation of 5-{N-[4-(2,2-diphenylvinyl)phenyl]-N-phenylamino}acenaphthene (Compound No. 1)

2.80 g (0.008 mol) of 5-[N-(4-formylphenyl)-N-phenylamino]acenaphthene and 3.04 g (0.01 mol) of diethyl diphenylmethylphosphonate were dissolved in 50 ml of N,N-dimethylformamide, and 1.35 g (0.012 mol) of potassium-tert-butoxide was added thereto for 20 minutes. After the addition, the resultant mixture was further stirred for 2 hours. The reaction was determined to be finished when disappearance of the formyl compound was identified. The reaction product was poured into 300 ml of methanol at a temperature of 5° C. or lower, and 30 ml of water was further dropwise added thereto to precipitate a crystal, and the crystal thus obtained was filtrated, washed with methanol and dried to obtain 3.38 g (yield: 84.6%) of a crystal. 3.0 g of the crystal thus obtained was purified by column chromatography (carrier: silica gel, eluent: toluene/hexane=¼) to obtain 2.30 g (purification yield: 76.7%, melting point: 189.0°–190.5° C.) of 5-{N-[4-(2,2-diphenylvinyl)phenyl]-N-phenylamino}acenaphthene (Compound No. 1).

According to elemental analysis, the product thus obtained was expressed by $C_{38}H_{29}N$, and the respective analytical values were carbon: 91.39% (91.35%), hydrogen: 5.73% (5.85%) and nitrogen: 2.91% (2.80%) (the values in the parentheses are calculation values).

Characteristic group wave numbers ($cm^{-1}$) according to infrared absorption spectrum (KBr tablet method) were 3024, 2914, 1584, 1487, 1292, 695, etc.

PREPARATION EXAMPLE 2 (Preparation of Compound No. 4)

Preparation of 5-{N-[4-(4-methylstyryl)phenyl]-N-phenylamino}acenaphthene 20.96 g (0.06 mol) of 5-[N-(4-formylphenyl)-N-phenylamino]acenaphthene prepared in Preparation Example 1 and 17.44 g (0.072 mol) of diethyl 4-methylbenzyl phosphonate were dissolved in 300 ml of N,N-dimethylformamide, and 10.1 g (0.09 mol) of potassium-tert-butoxide was added thereto at room temperature for 20 minutes. After the addition, the resultant mixture was further stirred for 2 hours. The reaction was determined to be finished when disappearance of the formyl compound was identified. The reaction product was poured into 1500 ml of methanol at a temperature of 5° C. or lower, and 150 ml of water was further dropwise added thereto to precipitate a crystal, which was then filtrated, washed with methanol and dried to obtain 22.18 g (yield: 84.5%) of a crude crystal. 21.0 g of the crude crystal thus obtained was purified by column chromatography (carrier: silica gel, eluent: toluene/hexane=¼) to obtain 17.85 g of (purification yield: 85.0%, melting point: 148.0°–149.0° C.) of 5-{N-[4-(4-methylstyryl)phenyl]-N-phenylamino}acenaphthene (Compound No. 4).

According elemental analysis, the product was expressed by $C_{33}H_{27}N$, and the analytical values were carbon: 90.49% (90.58%), hydrogen: 6.30% (6.22%) and nitrogen: 3.02% (3.20%) (the values in the parentheses are calculation values).

Characteristic group wave numbers ($cm^{-1}$) according to infrared absorption spectrum (KBr tablet method) were 3022, 2914, 1586, 1487, 1304, 694, etc.

PREPARATION EXAMPLE 3 (Preparation of Compound No. 5)

Preparation of 5-(N-acetylamino)acenaphthene 50 ml of glacial acetic acid was added to 6.77 g (0.04 mol) of 5-aminoacenaphthene and the mixture was stirred at 60° C. to dissolve, and 8.16 g (0.08 mol) acetic anhydride was dropwise added thereto for 15 minutes. After finishing the dropwise addition, the mixture was stirred at the same temperature for 2 hours. The reaction was determined to be finished when disappearance of 5-aminoacenaphthene was identified. The reaction product was poured into 500 ml of ice water to precipitate a crystal, which was then filtrated, washed with water and dried. As this result, 8.15 g (yield: 96.4%, melting point: 180.0°–186.0° C.) of 5-(N-acetylamino)acenaphthene was obtained.

Preparation of 5-[N-(4-tolyl)amino]acenaphthene 7.39 g (0.035 mol) of the above prepared 5-(N-acetylamino)acenaphthene was mixed with 10.91 g (0.05 mol) of p-iodo toluene, 0.32 g (0.005 mol) of copper powder, 5.52 g (0.04 mol) of anhydrous potassium carbonate and 10 ml of nitrobenzene, and the mixture was stirred at 200° C. for 6 hours. The reaction was determined to be finished when disappearance of 5-(N-acetylamino) acenaphthene was identified. To the resultant reaction mixture, was added an aqueous solution having 10 ml of isoamyl alcohol and 9.8 g (0.15 mol) of 85% potassium hydroxide dissolved in 10 ml of water, and the resultant mixture was subjected to hydrolysis reaction at 130°–140° C. for 4 hours. After identifying the end of the hydrolysis reaction, 100 ml of water was added thereto, and isoamyl alcohol and nitrobenzene were distilled off by azeotropic distillation. 100 ml of toluene was then added to the remaining material to dissolve the reaction product, and the toluene layer was separated. The toluene layer was washed with 100 ml of water, and was concentrated. An oily product thus obtained was purified by column chromatography (carrier: silica gel, eluent: toluene/hexane=¼). As this result, 6.56 g (yield: 72.3%, melting point: 96.2°–96.8° C.) of 5-[N-(4-tolyl)amino]acenaphthene was obtained.

Preparation of 5-[N-(4-tolyl)-N-phenylamino]acenaphthene 4.66 g (0.018 mol) of the above prepared 5-[N-(4-tolyl)amino]acenaphthene was mixed with 4.99 g (0.022 mol) of iodo benzene, 0.13 g (0.002 mol) of copper powder, 2.76 g (0.02 mol) of anhydrous potassium carbonate and 5 ml of nitrobenzene, and the resultant mixture was stirred at 200° C. for 25 hours. The reaction was determined to be finished when disappearance of 5-[N-(4-tolyl)amino]acenaphthene was identified. 100 ml of toluene was added thereto to dissolve the reaction product, and the mixture was filtrated and concentrated. The concentrated material thus obtained was purified by column chromatography (carrier: silica gel, eluent: toluene/hexane=¼) to obtain 5.06 g (yield: 83.8%, melting point: 147.0°–148.0° C.) of 5-[N-(4-tolyl)-N-phenylamino]acenaphthene.

Preparation of 5-[N-(4-formylphenyl)-N-(4-tolyl) amino]acenaphthene 4.7 g (0.014 mol) of the above prepared 5-[N-(4-tolyl)-N-phenylamino]acenaphthene was dissolved in 30 ml of N,N-dimethylformamide, and 3.22 g (0.021 mol) of phosphorus oxychloride was dropwise added thereto at room temperature for 10 minutes. After the temperature was raised to 50° C., and the mixture was stirred for 14 hours. The reaction was determined to be finished when disappearance of 5-[N-(4-tolyl)-N-phenylamino]acenaphthene was identified. The reaction product was poured into an aqueous solution having 10 g (0.23 mol) of 93% sodium hydroxide dissolved in 250 ml of water. The resultant mixture was cooled to precipitate a crystal, which was then filtrated, washed with water and dried to obtain 4.94 g (yield: 97.1%) of 5-[N-(4-formylphenyl)-N-(4-tolyl)amino]acenaphthene.

Preparation of 5-{N-[4-(4-methylstyryl)phenyl]-N-(4-tolyl)amino}acenaphthene (Compound No. 5)

4.36 g (0.12 mol) of the above prepared 5-[N-(4-formylphenyl)-N-(4-tolyl)amino]acenaphthene and 3.88 g (0.016 mol) of diethyl 4-methylbenzylphosphonate were dissolved in 40 ml of N,N-dimethylformamide, and 2.02 g (0.018 mol) of potassium-tert-butoxide was added thereto at room temperature for 10 minutes. After the addition, the mixture was further stirred for 2 hours. The reaction was determined to be finished when disappearance of the formyl compound was identified. The reaction product was poured into 200 ml of methanol at a temperature of 5° C. or lower, and 50 ml of water was dropwise added thereto to precipitate a crystal, which was then filtrated, washed with methanol and dried to obtain 4.44 g of (yield: 81.9%) of a crystal. 4.0 g of the crystal thus obtained was purified by column chromatography (carrier: silica gel, eluent: toluene/hexane= ¼) to obtain 3.63 g (purification yield: 90.8%, melting initiation temperature: 87.5° C.) of 5-{N-[4-(4-methylstyryl) phenyl]-N-(4-tolyl)amino}acenaphthene (Compound No. 5).

According to elemental analysis, the product was expressed by $C_{34}H_{29}N$, and the analytical values were carbon, 90.51% (90.42%), hydrogen: 6.51% (6.47%) and nitrogen: 2.98% (3.10%) (the values in the parentheses are calculation values).

Characteristic group wave numbers ($cm^{-1}$) according to infrared absorption spectrum (KBr tablet method) were 3020, 2916, 1594, 1503, 1310, 818, etc.

PREPARATION EXAMPLE 4 (Preparation of Compound No. 14)

Preparation of 5-{N-[4-(4-methylstyryl)phynel]-N-(4-formylphenyl)amino}acenaphthene 17.5 g (0.04 mol) of 5-{N-[4-(4-methylstyryl) phenyl]-N-phenylamino}acenaphthene prepared in Preparation Example 2 was dissolved in 150 ml of N,N-dimethylformamide, and 9.09 g (0.06 mol) of phosphorus oxychloride was dropwise added thereto at room temperature for 40 minutes. The temperature was raised to 50° C. and the mixture was stirred for 22 hours. The reaction was determined to be finished when disappearance of 5-{N-[4-(4-methylstyryl)phenyl]-N-phenylamino}acenaphthene was identified. The reaction product was poured into an aqueous solution having 23 g (0.53 mol) of 93% sodium hydroxide dissolved in 1000 ml of water. The reaction mixture was then cooled to precipitate a crystal, which was then filtrated, washed with water, washed with methanol and dried to obtain 17.66 g (yield: 94.8%) of a crystal. 16.0 g of the crystal thus obtained was purified by column chromatography (carrier: silica gel, eluent: toluene/hexane=1/1) to obtain a 12.05 g (yield: 75.3%, melting point: 105.0°–108.0° C.) of 5-{N-[4-(4-methystyryl) phenyl]-N-(4-formylphenyl) amino}acenaphthene.

Preparation of 5-{N-[4-(4-methylstyryl)phenyl]-N-[4-(2,2-diphenylvinyl)phenyl]amino}}acenaphthene (Compound No. 14)

4.66 g (0.01 mol) of the above prepared 5-{N-[4-(4-methylstyryl) phenyl]-N-(4-formylphenyl) amino}acenaphthene and 4.56 g (0.015 mol) of diethyl diphenylmethylphosphonate were dissolved in 40 ml of N,N-dimethylformamide, and 2.02 g (0.018 mol) of potassium-tert-butoxide was added thereto at room temperature for 10 minutes. After the addition, the mixture was further stirred for 2 hours. The reaction was determined to be finished when disappearance of the formyl compound was identified. The reaction product was poured into 400 ml of methanol at a temperature of 5° C. or lower, 40 ml of water was further dropwise added thereto to precipitate a crystal, which was then filtrated, washed with methanol and dried to obtain 4.9 g (yield: 79.7%) of a crystal. 4.5 g of the crystal thus obtained was purified by column chromatography (carrier: silica gel, eluent: toluene/hexane=¼) to obtain 3.83 g (purification yield: 85.2%, melting initiation point: 102.0° C.) of 5-{N[4-(4-methystyryl)phenyl]-N-[4-(2,2-diphenylvinyl) phenyl]amino}acenaphthene (Compound No. 14).

According to elemental analysis, the product was expressed by $C_{47}H_{37}N$, and the analytical values were carbon: 91.49% (91.67%), hydrogen: 6.18% (6.06%) and nitrogen: 2.33% (2.28%) (the values in the parentheses are calculation values).

Characteristic group wave numbers ($cm^{-1}$) according to infrared absorption spectrum (KBr tablet method) were 3020, 2916, 1590, 1500, 1306, 698, etc.

PREPARATION EXAMPLE 5 (Synthesis of Compound No. 15)

5-[4,4'-bis(4-methylstyryl)diphenylamino] acenaphthene 4.66 g (0.01 mol) of 5-{N-[4-(4-methylstyryl)phenyl]-N-(4-formylphenyl)amino}acenaphthene prepared in Preparation Example 4 and 2.91 g (0.012 mol) diethyl 4-methylbenzylphosphonate were dissolved in 40 ml of N,N-dimethylformamide, and 1.68 g (0.015 mol) of potassium-tert-butoxide was added thereto for 10 minutes. After the addition, the mixture was further stirred for 2 hours. The reaction was determined to be finished when disappearance of the formyl compound was identified. The reaction product was poured into 400 ml of methanol at a temperature of 5° C. or lower, and 40 ml of water was further dropwise added thereto to precipitate a crystal, which was then filtrated, washed with methanol and dried to obtain 5.1 g (yield: 92.3%) of a crystal. 5.0 g of the crystal thus obtained was purified by column chromatography (carrier: silica gel, eluent: toluene/hexane=¼) to obtain 4.19 g (purification yield: 83.8%, melting initiation point: 101.5° C.) of 5-[4,4'-bis(4-methylstyryl)diphenylamino] acenaphthene (Compound No. 15).

According to elemental analysis, the product was expressed by $C_{42}H_{35}N$, and the analytical values were carbon: 91.35% (91.10%), hydrogen: 6.25% (6.37%) and nitrogen: 2.40% (2.53%) (the values in the parentheses are calculation values).

Characteristic group wave numbers ($cm^{-1}$) according to infrared absorption spectrum (KBr tablet method) were 3020, 2916, 1591, 1504, 1306, 821, etc.

EXAMPLE 1

As a charge-generating material, 1.5 parts by weight of the following Chlorodiane Blue (charge-generating material No. 1):

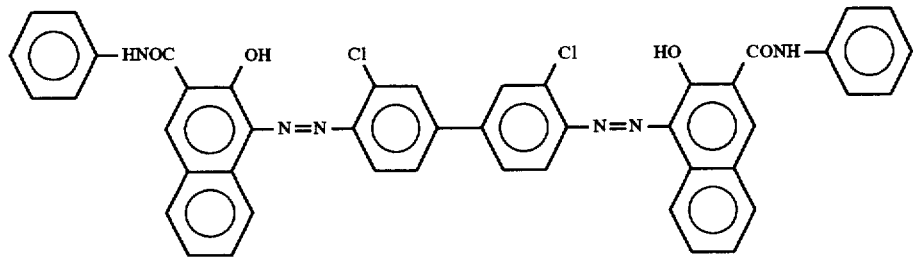

was added to 18.5 parts by weight of a 8% THF solution of a polyester resin (Viron 200, manufactured by Toyobo Co., Ltd.), and the mixture was put in an agate pot containing agate balls and rotated and dispersed for one hour by a planetary pulverizer (manufactured by Fritsch Co.). The obtained dispersion was coated on an aluminum surface of an aluminum-vapor deposited PET film as an electrically conductive support, by means of a wire bar coater and dried for 2 hours at 60° C. under atmospheric pressure and further for 2 hours under reduced pressure to form a charge-generating layer having a thickness of 0.3 μm.

On the other hand, as a charge-transporting material, 1.5 parts by weight of an acenaphthene compound of Compound No. 1 was added to 18.75 parts by weight of a 8% dichloroethane solution of a polycarbonate resin (Panlite K-1300, manufactured by Teijin Kasei K. K.), and the mixture was subjected to supersonic waves to completely dissolve the acenaphthene compound. This solution was coated on the above-mentioned charge-generating layer by a wire bar coater and dried for 2 hours at 60° C. under atmospheric pressure and further for 2 hours under reduced pressure to form a charge-transporting layer having a thickness of about 20 μm, to obtain photoreceptor No. 1.

With respect to this photoreceptor, the sensitivity was measured by means of an electrostatic copy paper testing apparatus ("EPA-8100" tradename, manufactured by Kawaguchi Denki Seisakusho K. K.). Firstly, the photoreceptor was electrified by corona discharge of −8 kV in a dark place, and then subjected to exposure with a white light of 3.0 lux, whereby the time (seconds) until the surface potential decreased to one half of the initial surface potential, was measured, to obtain a half value exposure El/2 (lux·sec). The initial surface potential of this photoreceptor was −1035 V, and El/2 was 0.82 lux·sec.

EXAMPLES 2 to 15

Photoreceptors No. 2 to No. 15 were prepared in the same manner as in Example 1 except that the charge-generating material and the charge-transporting material (acenaphthene compound) used in Example 1 were changed to those shown in Table 1.

The structures of charge-generating materials No. 2 to No. 4 shown in Table 1 will be shown below. Charge-generating material No. 2

Charge-generating material No. 2

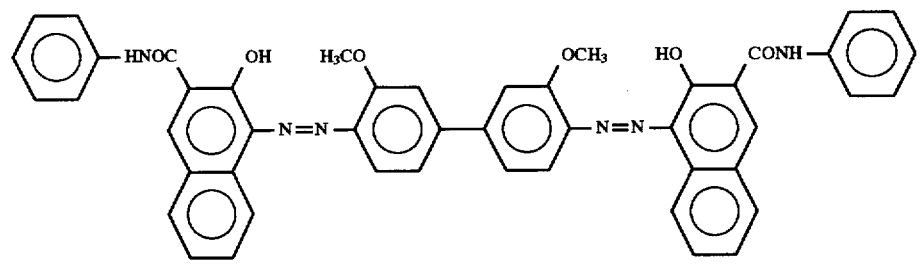

Charge-generating material No. 3

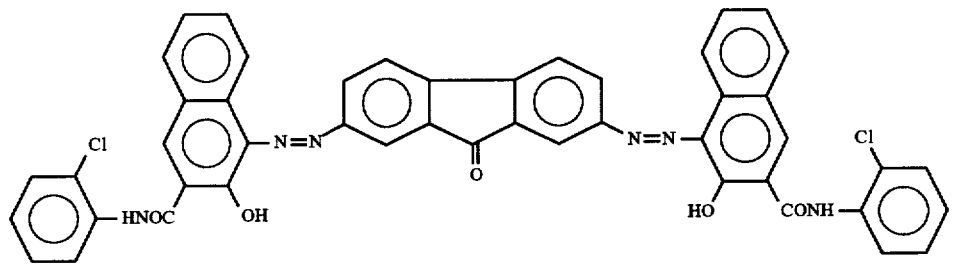

Charge-generating material No. 4

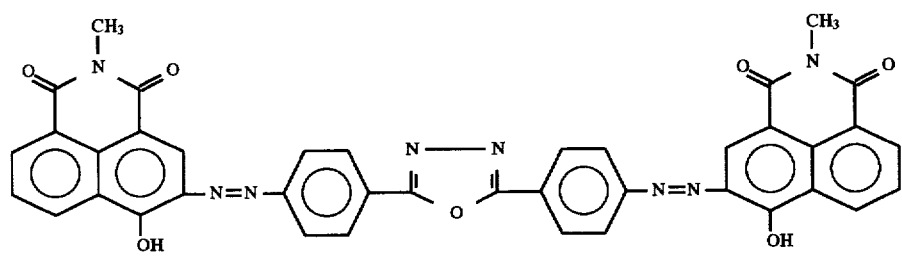

With respect to photoreceptors No. 2 to No. 15, the sensitivities were measured in the same manner as in Example 1. The results are shown in Table 2.

TABLE 1

| Example No. | Photoreceptor No. | Charge-transporting material (Compound No.) | Charge-generating material No. |
|---|---|---|---|
| 2 | 2 | 2 | 3 |
| 3 | 3 | 3 | 1 |
| 4 | 4 | 4 | 3 |
| 5 | 5 | 5 | 3 |
| 6 | 6 | 6 | 2 |
| 7 | 7 | 7 | 2 |
| 8 | 8 | 8 | 2 |
| 9 | 9 | 9 | 2 |
| 10 | 10 | 10 | 1 |
| 11 | 11 | 11 | 3 |
| 12 | 12 | 12 | 3 |
| 13 | 13 | 13 | 4 |
| 14 | 14 | 14 | 4 |
| 15 | 15 | 15 | 1 |

TABLE 2

| Photoreceptor No. | Initial surface potential (−volt) | El/2 (lux.sec) |
|---|---|---|
| 2 | 1053 | 0.83 |
| 3 | 970 | 0.91 |
| 4 | 957 | 0.78 |
| 5 | 1022 | 0.78 |
| 6 | 988 | 0.97 |
| 7 | 1013 | 0.88 |
| 8 | 1058 | 1.01 |
| 9 | 962 | 0.90 |
| 10 | 1007 | 0.94 |
| 11 | 1081 | 1.04 |
| 12 | 1034 | 1.05 |
| 13 | 994 | 0.83 |
| 14 | 1016 | 0.86 |
| 15 | 986 | 0.79 |

EXAMPLE 16

Photoreceptor No. 16 was prepared in the same manner as in Example 1 except that the charge-transporting material (acenaphthene compound) used in Example 1 was changed to a mixture of an acenaphthene compound of Compound No. 1 and an acenaphthene compound of Compound No. 4 in a weight ratio of 1:1. With respect to this photoreceptor, the sensitivity was measured in the same manner as in Example 1, whereby the initial surface potential was −1010V, and El/2 was 0.79 lux·sec.

EXAMPLE 17

As a charge-generating material, 1.5 parts by weight of α-TiOPc was added to 50 parts by weight of a 3% THF solution of a polyvinylbutyral resin (Esrec BX-L, manufactured by Sekisui Chemical Co., Ltd.), and the mixture was dispersed for 45 minutes by a supersonic disperser. The obtained dispersion was coated on an aluminum surface of an aluminum-vapor deposited PET film as an electrically conductive support, by means of a wire bar coater and dried for 2 hours at 60° C. under atmospheric pressure and further for 2 hours under reduced pressure to form a charge-generating layer having a thickness of 0.2 μm.

On the other hand, as a charge-transporting material, 1.5 parts by weight of an acenaphthene compound of Compound No. 1 was added to 18.75 parts by weight of a 8% dichloroethane solution of a polycarbonate resin (Panlite K-1300, manufactured by Teijin Kasei K. K.), and subjected to supersonic waves to completely dissolve the acenaphthene compound. This solution was coated on the above charge-generating layer by a wire bar coater and dried for 2 hours at 60° C. under atmospheric pressure and further for 2 hours under reduced pressure to form a charge-transporting layer having a thickness of about 20 μm, to obtain a photoreceptor No. 17.

With respect to this photoreceptor, the sensitivity was measured by means of an electrostatic copy paper testing apparatus ("EPA-8100", tradename). Firstly, the photoreceptor was electrified by a corona discharge of −8 kV in a dark place and then subjected to exposure with monochromatic light of 800 nm at a dose of 1.0 μW/cm², whereby the energy until the surface potential decreased to one half of the initial surface potential was determined to obtain a half value exposure El/2 (μJ/cm²). The initial surface potential of this photoreceptor was −989 V, and El/2 was 0.59 μJ/cm².

EXAMPLE 18

Photoreceptor No. 18 was prepared in the same manner as in Example 17 except that as a charge-generating material, the following trisazo compound:

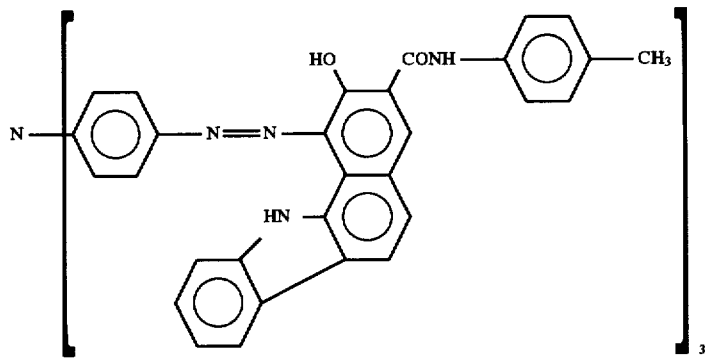

was used instead of α-TiOPc. With respect to this photoreceptor, the sensitivity was measured in the same manner as in Example 17, whereby the initial surface potential was −1037 V, and El/2 was 0.54 μJ/cm².

EXAMPLE 19

0.1 part by weight of the following thiapyrylium salt:

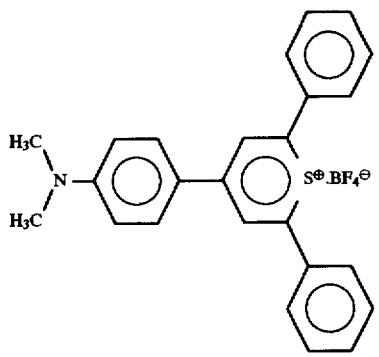

as a charge-generating material and 10 parts by weight of an acenaphthene compound of Compound No. 5 as a charge-transporting material were added to 125 parts by weight of a 8% dichloroethane solution of a polycarbonate resin (Panlite K-1300, manufactured by Teijin Kasei K. K.), and supersonic waves were applied to completely dissolve the thiapyrylium salt and the acenaphthene compound. This solution was coated on an aluminum surface of an aluminum-vapor deposited PET film as an electrically conductive support, by means of a wire bar coater and dried for 2 hours at 60° C. under atmospheric pressure and further for 2 hours under reduced pressure to form a photosensitive layer having a thickness of 20 μm, to obtain photoreceptor No. 19.

With respect to this photoreceptor, the sensitivity was measured by means of an electrostatic copy paper testing apparatus ("EPA-8100", tradename). Firstly, the photoreceptor was electrified by a corona discharge of +8 kV in a dark place and then subjected to exposure with a white light of 3.0 lux, whereby the time (seconds) until the initial surface potential decreased to one half, was measured to obtain a half value exposure El/2 (lux·sec). The initial surface potential of this photoreceptor was +927 V, and El/2 was 1.4 lux·sec.

EXAMPLE 20

The coating solution of a charge-transporting material used in Example 1, was coated on an aluminum surface of an aluminum-vapor deposited PET film by means of a wire bar coater and dried for 2 hours at 60° C. under atmospheric pressure and further for 2 hours under reduced pressure to form a charge-transporting layer having a thickness of 10 μm.

On the other hand, as a charge-generating material, 3.0 parts by weight of the same disazo compound as used in Example 2 was added to 18.5 parts by weight of a 8% THF solution of a polyester resin (Viron 200, manufactured by Toyobo Co., Ltd.), and the mixture was put into an agate pot containing agate balls and rotated and dispersed for one hour by a planetary pulverizer (manufactured by Fritsch Co.). To this dispersion, 200 ml of THF was added, followed by stirring to obtain a coating solution. This coating solution was spray-coated on the above charge-transporting layer and dried for 2 hours at 60° C. under atmospheric pressure and further for 2 hours under reduced pressure to form a charge-generating layer having a thickness of 0.5 μm. Further, a solution having an alcohol-soluble polyamide resin dissolved in isopropanol, was spray-coated on this charge-generating layer and dried for 2 hours at 60° C. under atmospheric pressure and further for 2 hours under reduced pressure to form an overcoating layer having a thickness of 0.5 μm, to obtain photoreceptor No. 20.

With respect to this photoreceptor, the sensitivity was measured in the same manner as in Example 1. The initial surface potential of this photoreceptor was +863 V, and El/2 was 1.2 lux·sec.

COMPARATIVE EXAMPLE 1

A comparative photoreceptor was prepared in the same manner as in Example 1, except that the acenaphthene compound of Compound No. 1 was replaced by the following compound.

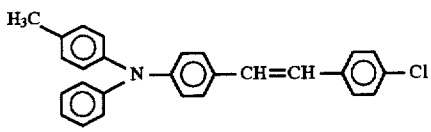

With respect to this photoreceptor, the sensitivity was measured in the same manner as in Example 1. The initial surface potential of this photoreceptor was −930 V, and E1/2 was 1.15 lux·sec.

Novel acenaphthene compounds of the present invention have an excellent charge-transporting ability, and the electrophotographic photoreceptor of the present invention having a photosensitive layer containing such a compound on an electrically conductive support, shows excellent properties as a photoreceptor, such as high sensitivity and high durability and thus has a merit that it can widely be used as a electrophotographic photoreceptor.

What is claimed is:

1. A electrophotographic photoreceptor, comprising a photosensitive layer which comprises a sensitizing dye, a binder resin and an acenaphthene derivative of formula (I):

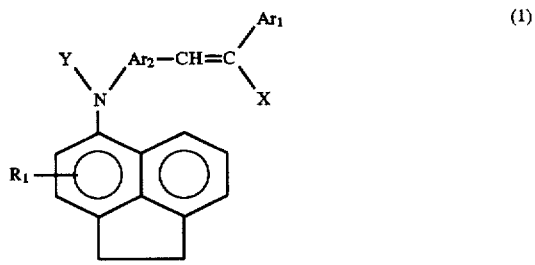

wherein $Ar_1$ is an unsubstituted or substituted aryl group;

$Ar_2$ is an unsubstituted or substituted phenylene, naphthylene, biphenylene or anthrylene group;

$R_1$ is a hydrogen atom, a lower alkyl group or a lower alkoxy group;

X is a hydrogen atom, an unsubstituted or substituted alkyl group or an unsubstituted or substituted aryl group; and Y is an unsubstituted or substituted aryl group or a group of the formula (2):

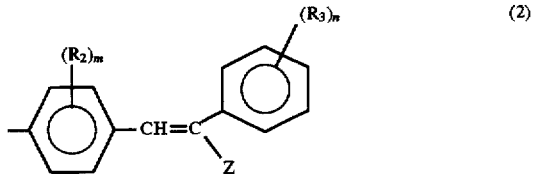

wherein $R_2$ is a hydrogen atom, a lower alkyl group or a lower alkoxy group, $R_3$ is a hydrogen atom, a halogen atom or a lower alkyl group, Z is a hydrogen atom or an unsubstituted or substituted aryl group, and m and n are, independently, an integer of from 0 to 4.

2. The electrophotographic photoreceptor of claim 1, wherein $Ar_1$ is substituted phenyl group, naphthyl group, biphenylyl group, anthryl group or pyrenyl group, wherein the substituent is selected from the group consisting of a halogen atom, a $C_{1-4}$ alkyl group, a $C_{1-4}$ alkyl group additionally substituted with a $C_{1-4}$ alkoxy group or a halogen atom, a $C_{1-4}$ alkoxy group, a $C_{1-4}$ alkoxy group additionally substituted with a $C_{1-4}$ alkoxy group or a halogen atom, a $C_{5-6}$ cycloalkyl group, a benzyl group, a benzyl group additionally substituted with a $C_{1-4}$ alkyl group, a $C_{1-4}$ alkoxy group or a halogen atom, a phenyl group and a phenyl group additionally substituted with a $C_{1-4}$ alkyl group, a $C_{1-4}$ alkoxy group or a halogen atom.

3. The electrophotographic photoreceptor of claim 1, wherein $Ar_2$ is substituted and the substituent is selected from the group consisting of halogen atom, a $C_{1-4}$ alkyl group, $C_{1-4}$ alkyl group additionally substituted with a $C_{1-4}$ alkoxy group or a halogen atom, a $C_{1-4}$ alkoxy group and a $C_{1-4}$ alkoxy group additionally substituted with a $C_{1-4}$ alkoxy group or a halogen atom.

4. The electrophotographic photoreceptor of claim 1, wherein $R_1$ is a hydrogen atom, a $C_{1-4}$ alkyl group or a $C_{1-4}$ alkoxy group.

5. The electrophotographic photoreceptor of claim 1, wherein X is a substituted alkyl group, wherein the substituent is selected from the group consisting of a $C_{1-4}$ alkoxy group, a $C_{5-6}$ cycloalkyl group and a halogen atom; or X is a substituted phenyl group, naphthyl group, biphenylyl group, anthryl group or pyrenyl group, wherein the substituent is selected from the group consisting of a halogen atom, a $C_{1-4}$ alkyl group, a $C_{1-4}$ alkyl group additionally substituted with a $C_{1-4}$ alkoxy group or a halogen atom, a $C_{1-4}$ alkoxy group, a $C_{1-4}$ alkoxy group additionally substituted with a alkoxy group or a halogen atom, a $C_{5-6}$ cycloalkyl group, a benzyl group, a benzyl group additionally substituted with a $C_{1-4}$ alkyl group, a $C_{1-4}$ alkoxy group or a halogen atom, a phenyl group and a phenyl group additionally substituted with a $C_{1-4}$ alkyl group, a $C_{1-4}$ alkoxy group or a halogen atom.

6. The electrophotographic photoreceptor of claim 1, wherein Y is a substituted phenyl group, naphthyl group, biphenytyl group, anthryl group or a pyrenyl group, wherein the substituent is selected from the group consisting of a halogen atom, a $C_{1-4}$ alkyl group, a $C_{1-4}$ alkyl group additionally substituted with a $C_{1-4}$ alkoxy group or a halogen atom, a $C_{1-4}$ alkoxy group, a $C_{1-4}$ alkoxy group additionally substituted with a $C_{1-4}$ alkoxy group or a halogen atom, a $C_{5-6}$ cycloalkyl group, a benzyl group, a benzyl group additionally substituted with a $C_{1-4}$ alkyl group, a $C_{1-4}$ alkoxy group or a halogen atom, a phenyl group and a phenyl group additionally substituted with a $C_{1-4}$ alkyl group, a $C_{1-4}$ alkoxy group or a halogen atom.

7. The electrophotographic photoreceptor of claim 1, wherein Y is a group of the formula (2):

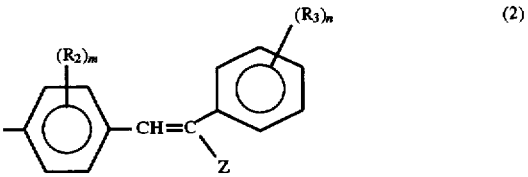

wherein $R_1$ is a hydrogen atom, a $C_{1-4}$ alkyl group or a $C_{1-4}$ alkoxy group;

$R_3$ is a hydrogen atom, a halogen atom or a $C_{1-4}$ alkyl group; and

Z is a halogen atom or a substituted phenyl group, naphthyl group, biphenylyl group, anthryl group or pyrenyl group, wherein the substituent is selected from the group consisting of a halogen atom, a $C_{1-4}$ alkyl group, a $C_{1-4}$ alkyl group additionally substituted with a $C_{1-4}$ alkoxy group or a halogen atom, a $C_{1-4}$ alkoxy group, a $C_{1-4}$ alkoxy group additionally substituted with a $C_{1-4}$ alkoxy group or a halogen atom, a $C_{5-6}$ cycloalkyl group, a benzyl group, a benzyl group additionally substituted with a $C_{1-4}$ alkyl group, a $C_{1-4}$ alkoxy group or a halogen atom, a phenyl group and a phenyl group additionally substituted with a $C_{1-4}$ alkyl group, a $C_{1-4}$ alkoxy group or a halogen atom.

8. A electrophotographic photoreceptor, comprising:
a charge generating material; and
a photosensitive layer comprising an acenapthene derivative of formula (I):

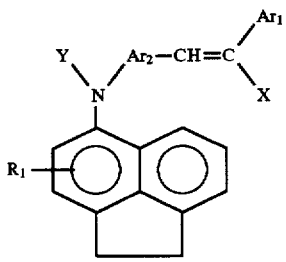
(1)

wherein
$Ar_1$ is an unsubstituted or substituted aryl group;
$Ar_2$ is an unsubstituted or substituted phenylene, naphthylene, biphenylene or anthrylene group;
$R_1$ is a hydrogen atom, a lower alkyl group or a lower alkoxy group;
X is a hydrogen atom, an unsubstituted or substituted alkyl group or an unsubstituted or substituted aryl group; and
Y is an unsubstituted or substituted aryl group or a group of the formula (2):

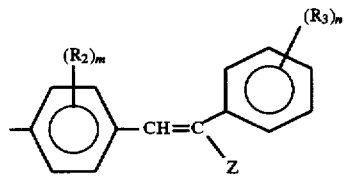
(2)

wherein
$R_2$ is a hydrogen atom, a lower alkyl group or a lower alkoxy group,
$R_3$ is a hydrogen atom, a halogen atom or a lower alkyl group,
Z is a hydrogen atom or an unsubstituted or substituted aryl group, and
m and n are, independently, an integer of from 0 to 4.

9. The electrophotographic photoreceptor of claim 8, wherein $Ar_1$ is substituted phenyl group, naphthyl group, biphenylyl group, anthryl group or pyrenyl group,
wherein the substituent is selected from the group consisting of a halogen atom, a $C_{1-4}$ alkyl group a $C_{1-4}$ alkyl group additionally substituted with a $C_{1-4}$ alkoxy group or a halogen atom, a $C_{1-4}$ alkoxy group, a $C_{1-4}$ alkoxy group additionally substituted with a $C_{1-4}$ alkoxy group or a halogen atom, a $C_{5-6}$ cycloalkyl group, a benzyl group, a benzyl group additionally substituted with a $C_{1-4}$ alkyl group, a $C_{1-4}$ alkoxy group or a halogen atom, a phenyl group and a phenyl group additionally substituted with a $C_{1-4}$ alkyl group, a $C_{1-4}$ alkoxy group or a halogen atom.

10. The electrophotographic photoreceptor of claim 8, wherein $Ar_2$ is substituted and the substituent is selected from the group consisting of halogen atom, a $C_{1-4}$ alkyl group, $C_{1-4}$ alkyl group additionally substituted with a $C_{1-4}$ alkoxy group or a halogen atom, a $C_{1-4}$ alkoxy group and a $C_{1-4}$ alkoxy group additionally substituted with a $C_{1-4}$ alkoxy group or a halogen atom.

11. The electrophotographic photoreceptor of claim 8, wherein $R_1$ is a hydrogen atom, a $C_{1-4}$ alkyl group or a $C_{1-4}$ alkoxy group.

12. The electrophotographic photoreceptor of claim 8, wherein X is a substituted alkyl group, wherein the substituent is selected from the group consisting of a $C_{1-4}$ alkoxy group, a $C_{5-6}$ cycloalkyl group and a halogen atom; or X is a substituted phenyl group, naphthyl group, biphenylyl group, anthryl group or pyrenyl group, wherein the substituent is selected from the group consisting of a halogen atom, a $C_{1-4}$ alkyl group, a $C_{1-4}$ alkyl group additionally substituted with a $C_{1-4}$ alkoxy group or a halogen atom, a $C_{1-4}$ alkoxy group, a $C_{1-4}$ alkoxy group additionally substituted with a $C_{1-4}$ alkoxy group or a halogen atom, a $C_{5-6}$ cycloalkyl group, a benzyl group, a benzyl group additionally substituted with a $C_{1-4}$ alkyl group, a $C_{1-4}$ alkoxy group or a halogen atom, a phenyl group and a phenyl group additionally substituted with a $C_{1-4}$ alkyl group, a $C_{1-4}$ alkoxy group or a halogen atom.

13. The electrophotographic photoreceptor of claim 8, wherein Y is a substituted phenyl group, naphthyl group, biphenylyl group, anthryl group or a pyrenyl group,
wherein the substituent is selected from the group consisting of a halogen atom, a $C_{1-4}$ alkyl group, a $C_{1-4}$ alkyl group additionally substituted with a $C_{1-4}$ alkoxy group or a halogen atom, a $C_{1-4}$ alkoxy group, a $C_{1-4}$ alkoxy group additionally substituted with a $C_{1-4}$ alkoxy group or a halogen atom, a $C_{5-6}$ cycloalkyl group, a benzyl group, a benzyl group additionally substituted with a $C_{1-4}$ alkyl group, a $C_{1-4}$ alkoxy group or a halogen atom, a phenyl group and a phenyl group additionally substituted with a $C_{1-4}$ alkyl group, a $C_{1-4}$ alkoxy group or a halogen atom.

14. The electrophotographic photoreceptor of claim 8, wherein Y is a group of the formula (2):

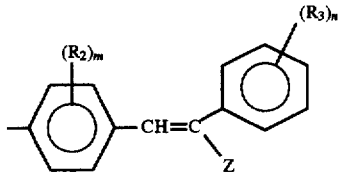
(2)

wherein
$R_2$ is a hydrogen atom, a $C_{1-4}$ alkyl group or a $C_{1-4}$ alkoxy group;
$R_3$ is a hydrogen atom, a halogen atom or a $C_{1-4}$ alkyl group; and
Z is a halogen atom or a substituted phenyl group, naphthyl group, biphenylyl group, anthryl group or pyrenyl group, wherein the substituent is selected from the group consisting of a halogen atom, a $C_{1-4}$ alkyl group, a $C_{1-4}$ alkyl group additionally substituted with a $C_{1-4}$ alkoxy group or a halogen atom, a $C_{1-4}$ alkoxy group, a $C_{1-4}$ alkoxy group additionally substituted with a $C_{1-4}$ alkoxy group or a halogen atom, a $C_{5-6}$ cycloalkyl group, a benzyl group, a benzyl group additionally substituted with a $C_{1-4}$ alkyl group, a $C_{1-4}$ alkoxy group or a halogen atom, a phenyl group and a phenyl group additionally substituted with a $C_{1-4}$ alkyl group, a $C_{1-4}$ alkoxy group or a halogen atom.

* * * * *